United States Patent

Johnson

Patent Number: 6,076,519
Date of Patent: *Jun. 20, 2000

[54] PASSIVE INSPIRATORY NEBULIZER SYSTEM

[75] Inventor: Robert J. Johnson, Riverside, Calif.

[73] Assignee: Ethex International, Inc., Riverside, Calif.

[*] Notice: This patent is subject to a terminal disclaimer.

[21] Appl. No.: 08/743,292

[22] Filed: Nov. 4, 1996

Related U.S. Application Data

[62] Division of application No. 08/166,694, Dec. 14, 1993, Pat. No. 5,570,682.

[51] Int. Cl.[7] ............................................. A61M 11/00
[52] U.S. Cl. ............................ 128/200.14; 128/200.16; 128/203.12; 128/204.23; 128/204.26
[58] Field of Search ...................... 128/200.14, 200.16, 128/200.18, 202.27, 203.12, 204.23, 204.26, 912, 205.11; 285/124.1, 124.3, 124.5, 123.1, 123.15

[56] References Cited

U.S. PATENT DOCUMENTS

| | | | |
|---|---|---|---|
| 515,504 | 2/1894 | Scharling | 128/200.14 |
| 533,489 | 2/1895 | Ogram | 128/200.14 |
| 724,675 | 4/1903 | Decker | 285/124.1 |
| 2,280,140 | 4/1942 | Wilson | 285/124.1 |
| 3,291,508 | 12/1966 | Kolothoff, Jr. | 285/124.1 |
| 3,301,255 | 1/1967 | Thompson | 128/200.18 |
| 3,598,116 | 8/1971 | Peters et al. | 128/200.18 |
| 3,664,337 | 5/1972 | Lindsey et al. | 128/200.18 |
| 3,826,255 | 7/1974 | Harstad et al. | 128/200.18 |
| 3,831,596 | 8/1974 | Cavallo | 128/204.23 |
| 3,885,820 | 5/1975 | Trumbull et al. | 285/124.5 |
| 4,036,253 | 7/1977 | Fegan et al. | 128/205.11 |
| 4,106,503 | 8/1978 | Rosenthal et al. | 128/200.18 |
| 4,278,110 | 7/1981 | Price et al. | 137/805 |
| 4,357,936 | 11/1982 | Ellestad et al. | 128/204.23 |
| 4,381,002 | 4/1983 | Mon | 128/204.24 |
| 4,396,015 | 8/1983 | Johnson | 128/200.14 |
| 4,446,863 | 5/1984 | Rubin et al. | 128/912 |
| 4,457,303 | 7/1984 | Durkan | 128/204.24 |
| 4,637,384 | 1/1987 | Schroeder | 128/912 |
| 4,677,975 | 7/1987 | Edgar et al. | 128/200.14 |
| 4,832,012 | 5/1989 | Raabe et al. | 128/200.21 |
| 4,848,333 | 7/1989 | Waite | 128/205.11 |
| 5,080,093 | 1/1992 | Raabe et al. | 128/203.12 |
| 5,099,837 | 3/1992 | Russel, Sr. et al. | 128/204.26 |
| 5,193,532 | 3/1993 | Moa et al. | 128/912 |
| 5,570,682 | 11/1996 | Johnson | 128/200.14 |

OTHER PUBLICATIONS

Auerbach et al, A New Oxygen Cannula System using Intermittent–Demand Nasal Flow, Chest, 74:1, Jul. 1978, pp. 39–44.

Mon, The Design of a Fluidic Oxygen Intermittent–Demand Flow Device, Report No. HDL–TM–80–14, Harry Diamond Laboratories, Adelphi, MD. 20783, Mar. 1980, pp. 5–8.

*Primary Examiner*—Aaron J. Lewis
*Attorney, Agent, or Firm*—Stout, Uxa, Buyan & Mullins, LLP; Donald E. Stout

[57] ABSTRACT

A hand-held nebulizer system is provided which nebulizes during the patient's inspiration cycle only. The system includes a universal sensor port adapter which is adapted to fluidly connect an airway device with a sensor port of the system's source of pressurized gas in such a manner as to permit the patient to inhale and exhale atmospheric air, while permitting the use of standard airway devices. A unique valve arrangement is also provided in the device for supplying the pressurized gas which permits the system to be extremely sensitive to small pressure differentials, thereby ensuring that the system detects the respiratory cycle phases of even the weakest patients.

19 Claims, 2 Drawing Sheets

PASSIVE INSPIRATORY NEBULIZER SYSTEM

This is a division of application Ser. No. 08/166,694 filed Dec. 14, 1993, now U.S. Pat. No. 5,570,682.

BACKGROUND OF THE INVENTION

This invention relates to a hand-held nebulizer system for delivering aerosolized medication to a patient, and more particularly to a passive inspiratory nebulizer system which delivers aerosolized medication only during the inspiratory phase of the patient's respiratory cycle.

Nebulization utilizes the venturi principle to fracture liquid medications into a fine aerosol mist, which a patient inhales, thereby absorbing the active ingredients of the aerosol across the pulmonary membranes to effect the desired treatment. It is a standard strategy for the therapeutic application of medicinal aerosols for a wide range of pulmonary dysfunctions, including asthma, COPD, bronchitis, cystic fibrosis, croup, etc.

One therapy employed in the respiratory care field for many years is Intermittent Positive Pressure Breathing (IPPB). This approach utilizes a machine which delivers medicated aerosols upon a patient's inspiratory effort, entrained in a stream of pressurized gas. Included in the machine is a highly sensitive control device which senses inhalation by the patient, and the resulting negative air pressure (as referenced from the ambient atmospheric pressure), causing the machine to apply a positive pressure flow of air through a T-connection or the like to a mouthpiece to assist the patient during such inhalation phase of each breathing cycle. However, to stop the stream of pressurized gas, the patient must firmly enclose the mouthpiece with his lips and positively seal the system to avoid any leakage, thus allowing pressure to build in the system, shutting it off.

Many older patients are too tired or confused to be able to cooperate in this effort, and a mask has to be fitted and firmly held over their mouth and nose, covering them. Even when sick, tired, and confused, many patients struggle. Obviously, this is not popular with either patients or practitioners.

In contrast to the IPPB approach, state of the art hand-held nebulizers, powered by pressurized gas from an outlet on the wall behind a patient's bed, or by an oilless compressor, run continuously during the entire twelve to fifteen minutes necessary to complete the medicinal nebulization prescribed for treatment of the disorder suffered by the patient.

In good health, the ratio of the time necessary for inhalation to exhalation is 1:2. That is, if it takes one second to inhale, it takes two to exhale. The essence of the dysfunction of most types of lung disease is the destruction of the structural integrity of the small airways of the lung, leading to their collapse on exhalation, and prolonging the expiratory phase of the cycle. This dysfunctional ratio may be as much as 1:4 or 1:5. Since deposition of the fresh medicinal aerosol onto the pulmonary membranes can occur only during the inspiratory phase of the respiratory cycle, nebulization during the expiratory phase is wasted, being blown into the room. While this result is obviously wasteful in terms of cost, it also makes it very difficult to ascertain how much medication is actually being received by the patient, because an unknown amount is being blown to the atmosphere during exhalation, so that the patient is unlikely to receive the exact dose prescribed by the physician.

Another alternative therapy which attempts to solve this problem is discussed in the inventor's prior U.S. Pat. No. 4,396,015. A prior art IPPB machine is employed with a modified T-connection airway device which is open to atmosphere at one end, thereby permitting the patient to inhale from and exhale to atmosphere rather than in a pressurized environment. To accomplish this, the pressurized breathing tube utilized in the IPPB system is removed, but a sensor tube between the machine and the airway device remains, so that the machine can sense the negative pressure signalling the inhalation cycle and provide pressurized gas to the nebulizer, and conversely shut off that pressurized gas when positive pressure is sensed, signalling expiration. To accomplish the desired function, the sensor tube is smaller than the diameter of the expired gas outlet port in the T-connection, so that the airway device remains open to the atmosphere.

The approach taught in the '015 patent is a vast improvement over previous prior art modalities, permitting the treatment time to be greatly shortened, and the aerosolized medication to be more accurately delivered. However, a customized T-connection airway device is required, having specific unique guide tube structure to accommodate the sensor tube. Since standardized T-connection airway devices are widely available in the industry, it is a significant disadvantage to require a customized version, both in terms of cost and availability. It is desirable, particularly in a hospital setting, to be able to stock only standardized airway devices, which are widely used, rather than to have to stock specific devices configured for only one application.

Another problem with the '015 patent approach is that the prior art IPPB machines are not sufficiently sensitive to the relatively small pressure changes generated by a sick and weak patient's respiratory cycle to reliably shut off the pressurized gas flow during the expiration cycle and to ensure that it is restored at the onset of inspiration. Accordingly, what is needed is a new driver for the passive inspiratory nebulizer system which is sensitive to extremely small pressure changes, is compact and lightweight for maximum portability, and is comprised of reliable and durable components.

SUMMARY OF THE INVENTION

This invention provides a passive inspiratory nebulization system which nebulizes during inspiration only. Since the entire goal of the hand held nebulizer modality is the inhalation of therapeutic aerosols, nebulization during the expiratory phase wastes both medication and treatment time. Nebulization during inspiration only permits a lower dosage requirement, improves patient and therapist interaction, reduces treatment time to a few well-coached breaths, and allows the clinician to titrate the medication dosage as needed.

More specifically, the invention provides a system for delivering pressurized gas during the inspiratory phase and for preventing the delivery of pressurized gas to the patient during the expiratory phase of the patient's respiratory cycle. Two particularly advantageous features distinguish the inventive system over the system disclosed in U.S. Pat. No. 4,396,015. First, a standard T-connector airway device may be employed, rather than a customized version. Second, a new pressurized gas supply device, or driver unit, is utilized, which is much more sensitive and responsive to pressure changes resulting from a patient's respiration cycle, e.g. the transition between inhalation and exhalation.

The system comprises a pressurized gas supply device, and an airway device having a first port adapted to receive pressurized gas from the gas supply device, a second port adapted to receive a mouthpiece through which a patient may inhale and exhale, and a third port which is open to the atmosphere, with a fluid passage interconnecting the first, second, and third ports. Significantly, as noted supra, the airway device may comprise a standard state of the art T-connector, which are readily available in the respiratory device market.

An important advantage of the system is the use of a universal adapter device, or sensor port adapter, for coupling the third port of the airway device to a sensor port associated with the pressurized gas supply device. The adapter device permits the device to provide pressurized gas to the first port responsive to pressure variations generated by the patient's respiration cycle. It comprises a first end adapted for insertion into the third port of the airway device and a second end adapted to be coupled to the sensor port, and further comprises structure for ensuring that the third port remains open to atmosphere when the first adapter end is inserted therein.

In another aspect of the invention, an adapter device is provided for use in an apparatus for delivering pressurized gas to a patient during inhalation and for preventing delivery of pressurized gas to the patient during exhalation. The adapter device is adapted to couple an airway device to a sensor port associated with a pressurized gas supply source, and comprises a generally tubular element having a fluid passage extending therethrough. A fluid passage extends therethrough, and the tube has a connector end adapted for insertion into an expired gas outlet port in the airway device, and a sensor end adapted to be coupled to a proximal end of a fluid line, with the fluid line being adapted to be coupled at a distal end thereof with the sensor port. Finally, and most significantly, the adapter device includes structure for ensuring that the expired gas outlet port remains open to atmosphere when the connector end is inserted therein, so that the patient is able to breathe air at atmospheric pressure at all times. Preferably, the structure comprises a generally disk-shaped element circumscribing the tubular element between the sensor end and the connector end, wherein the disk-shaped element has at least one hole extending entirely therethrough, so that when the connector end is inserted into the expired gas outlet port, the disk-shaped element abuts the end of the airway device and the airway device is open to atmosphere through the at least one hole.

Yet another important aspect of the invention is the provision of a pressurized gas supply device, which includes a fluidic valve adapted to be actuated responsive to the patient's respiratory cycle, and a gas pressure driven on/off valve adapted to be actuated responsive to a gas flow from the fluidic valve at a pressure above a predetermined trigger pressure. The on/off valve is triggered by actuation of the fluidic valve to the on position to permit the flow of pressurized gas to the airway device first port only during the patient's inspiratory cycle.

The fluidic valve includes an element which moves responsive to pressure sensed at a sensor port in the driver unit, so that when the pressure sensed at the sensor port is below a predetermined pressure, indicating that the patient is inhaling, the fluidic valve element moves responsive thereto to open the fluidic valve and permit a flow of gas at the triggering pressure to enter the on/off valve, thereby opening the on/off valve and triggering a full flow of pressurized gas to exit the driver unit for delivery to the first port in the airway device.

The invention, together with additional features and advantages thereof, may best be understood by reference to the following description taken in connection with the accompanying illustrative drawing.

BRIEF DESCRIPTION OF THE DRAWING

FIG. 3 is a cross-sectional view of the sensor port adapter illustrated schematically in FIG. 1.

DESCRIPTION OF THE PREFERRED EMBODIMENT

Figure 1:
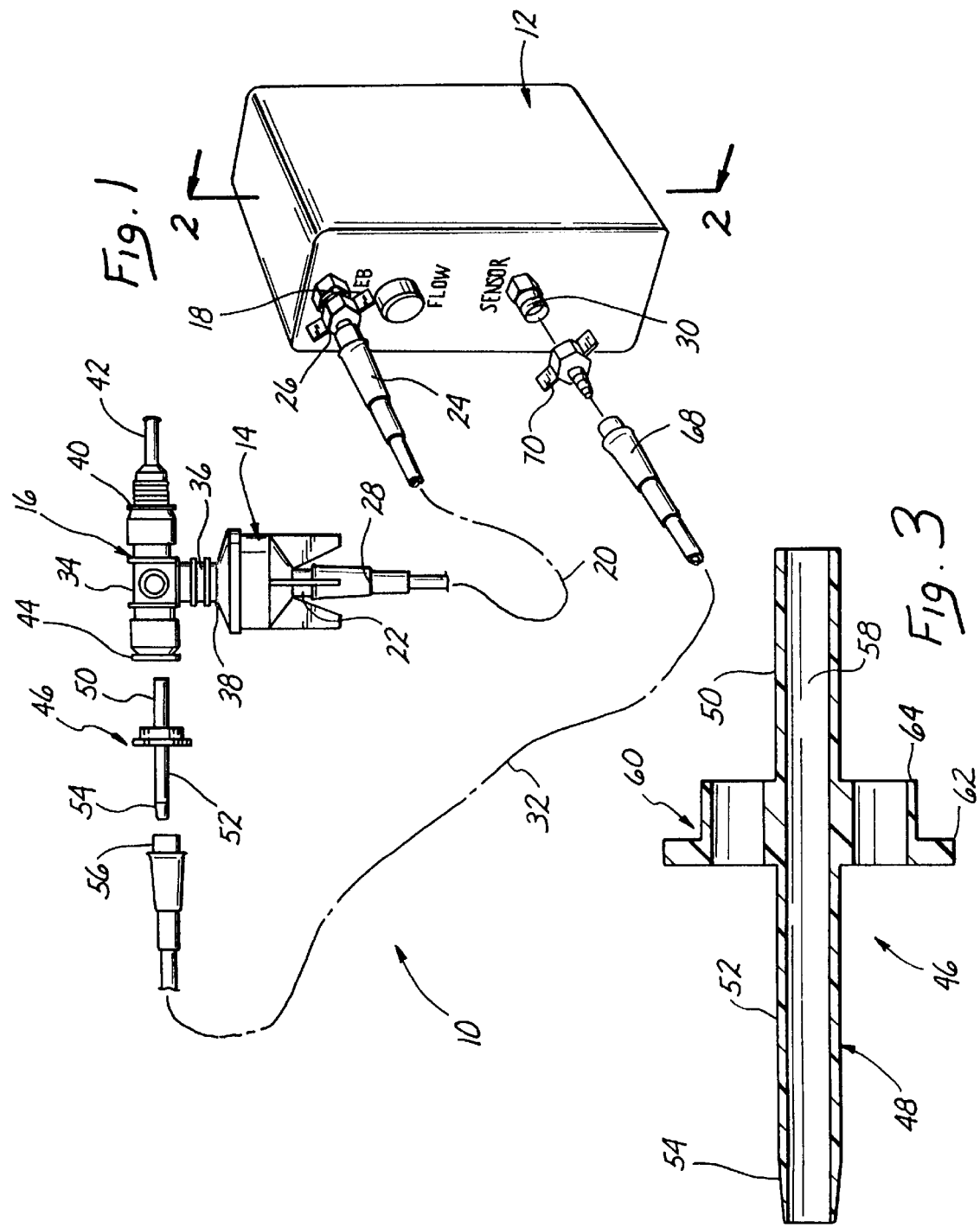
FIG. 1 is a schematic view of a passive inspiratory nebulizer system constructed in accordance with the teachings of the invention.

FIG. 1 illustrates a passive inspiratory nebulizer system 10 which comprises a system driver unit 12, a nebulizer unit 14, and a T-connection airway device 16. The driver unit 12 includes a nebulizer port 18, which is fluidly connectable by means of a first oxygen tube 20 to the nebulizer unit 14 through a nebulizer inlet 22. The oxygen tube 20 is preferably connected to the nebulizer port 18 using a standard fitting 24 and adapter 26, and is connected to the nebulizer inlet 22 by means of a standard fitting 28. The driver unit also includes a sensor port 30, which is similarly fluidly connectable by means of a second oxygen tube 32 to the airway device 16, in a manner described more fully hereinbelow.

The T-connection 16 is an airway device, standard in the art, which is preferably molded of transparent rigid plastic. It has a first hollow tubular portion 34 and a second hollow tubular portion 36 extending at substantially right angles to one another to form a T, each of the portions 34 and 36 enclosing fluid passages (not shown) which fluidly communicate at the T intersection. The nebulizer unit 14 communicates at its outlet end with the second tubular portion 36 of the airway device 16 through a first port 38. At one end of the first tubular portion 34 is a second port 40, into which a mouthpiece 42 is adapted to be inserted. At the opposite end of the first tubular portion 34 is a third port or expired gas outlet port 44, which is open to atmosphere and into which a sensor port adapter 46 may be inserted. This expired gas outlet port 44 is provided universally in state of the art hand held nebulizer T-connection airway devices, is substantially circular, and, in the preferred embodiment, has a diameter of about 22 mm, which is also a prior art standard.

Referring now to both FIGS. 1 and 3, the sensor port adapter 46 provides an interface between the expired gas outlet port 44 and the second oxygen tube 32. It comprises a hollow tubular element 48 which has a sensor end 50 and a connector end 52. The connector end has an extruded nipple 54, hollow down its center, which is adapted to slide into a fitting 56 on the airway device end of the second oxygen tube 32, such that there is an interference fit between the nipple 54 and the fitting 56. Thus, the sensor port adapter 46 serves to interconnect the oxygen tube 32 and the sensor port adapter 46. The hollow center of the tubular element 48, in conjunction with the hollow center of the extruded nipple 54, together comprise a continuous fluid passage 58. A flat annular disk 60, preferably made of plastic, surrounds the hollow tubular element 48 and is preferably molded integrally with the cylindrical outside wall thereof, serving to separate the sensor end 50 from the connector end 52. The disk 60 actually comprises a larger diameter disk portion 62 toward the connector end side of the tube 48, which preferably has a diameter just slightly larger than the diameter of the expired gas outlet port 44 (i.e. slightly more than 22 mm in the preferred embodiment), and a smaller diameter disk portion 64, which is integral with the larger diameter portion 62, toward the sensor end side of the tube 48. The diameter of the disk portion 64, which in the preferred embodiment has a greater axial length than the disk portion 62, is sized to be slightly smaller than the diameter of the passage 58, so that the connector end 52 may be inserted into the expired gas outlet port 44 and fluid passage 58 until the smaller diameter disk portion 64 is substantially flush within the end of the passage 58 and the larger diameter disk portion 62 abuts the end of the airway device 16. The disk 58 is perforated with a plurality of holes 64, which extend completely through both disk portions 60 and 62.

At its distal end, the oxygen tube 32 is adapted to be attached to the sensor port 30. This attachment may be made in any conventional fashion, such as by means of a standard fitting 68 and threaded adapter 70, as shown in FIG. 1.

Figure 2:
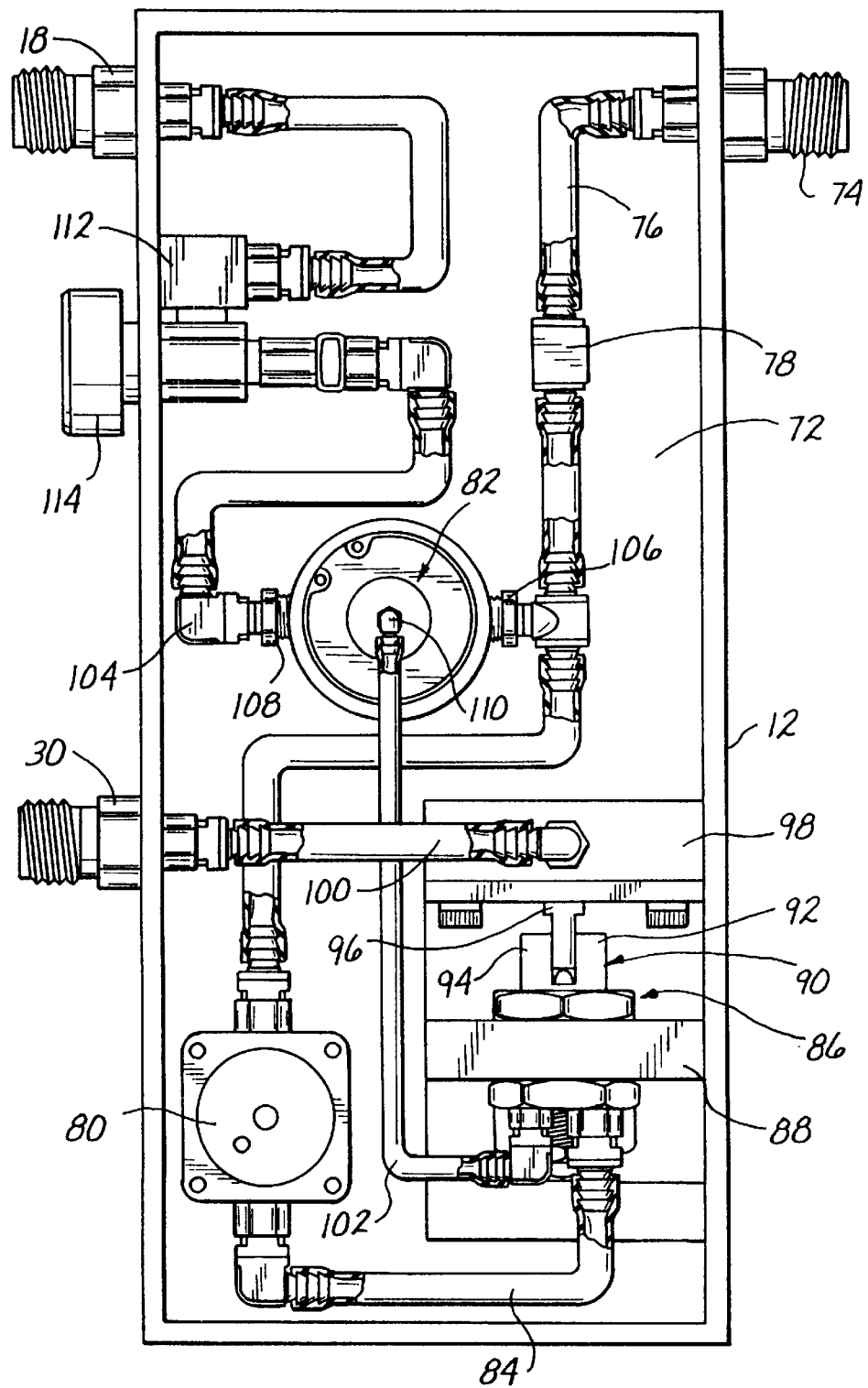
FIG. 2 is a schematic view of the interior of the driver for the passive inspiratory nebulizer system shown in FIG. 1, viewed along lines 2—2 of FIG. 1.

Referring now to FIG. 2, the interior of the driver 12 is illustrated. The interior 72 is preferably of a composite/plastic construction, with gas flow ducts machined appropriately therein. The exterior dimensions of the driver are designed to be as small as possible (6 in. by 4 in. by 2½ inches in the preferred embodiment), so that the driver, being both compact and constructed of lightweight materials, is as portable as possible.

The driver 12 comprises a medical gas inlet 74, for receiving medical quality gas from a source of supply, such as a wall outlet in a hospital room. The gas, which comprises oxygen or an air mixture, is typically delivered at about 55 PSI. Once delivered through the inlet 74, the gas flows through an inlet passage 76, passing through a filter 78 to ensure its purity before being inhaled by a patient. The filter 78 is preferably a 2 micron filter, standard in the art. The gas then travels through a flow regulator 80, which regulates the trigger pressure for a pneumatically actuated on/off valve 82, in a manner to be described more fully hereinbelow.

Once it exits the regulator 80, the regulated trigger gas flows through a gas passage 84 into a first stage fluidic valve 86. The fluidic valve 86 comprises a sensor adjustment bracket 88 and a sensor yoke 90, wherein the sensor yoke 90 has a pair of upstanding legs 92 and 94, respectively. Extending downwardly and between the two yoke legs 92 and 94 is a diaphragm tip or paddle 96, which is housed within a diaphragm housing 98. The diaphragm tip 96 is adapted to be actuated upwardly or downwardly in response to fluid pressure in a sensor passage 100 which communicates with the driver sensor port 30, so that when the pressure in the passage is higher than a level determined by an adjustment of the sensor adjustment bracket 88, the diaphragm tip 96 is pushed downwardly, thereby blocking a small metering aperture (not shown) in each of the sensor yoke legs 92 and 94. On the other hand, when the pressure in the passage 100 drops below this predetermined level, the diaphragm tip is pulled upwardly, thereby unblocking the two metering apertures. In this unblocked state, the regulated trigger gas is permitted to flow through the first yoke leg 92, exit the metering aperture therein, impinge on and enter the metering aperture in the second yoke leg 94, and subsequently exit the fluidic valve 86 via a trigger gas passage 102.

The pneumatically actuated on/off valve 82 is preferably a single-stage diaphragm-actuated valve and is arranged as an in-line valve in a gas line 104, which in turn communicates at a T-fitting 106 with the fluid passage 76 upstream of the flow regulator 80. One such valve is sold under the BOOSTER-MITE trademark. The BOOSTER-MITE valve includes a gas inlet 106, a gas outlet 108, and a trigger gas inlet 110. The default condition for the valve 82 is to be shut off, so that no gas is permitted to flow from the gas passage 76 through valve inlet 106 and outlet 108 into the gas line 104. However, when gas at a pressure above a predetermined trigger pressure enters the valve 82 through the trigger gas inlet 110, the gas pressure disrupts an established laminar gas flow, pushing that flow in another direction. This triggers a full flow of gas from the gas passage 76 through the inlet and outlet valve ports 106 and 108, respectively, and then through the gas line 104 to a flow valve 112. A flow control knob 114, actuated by either the patient or medical personnel, or perhaps even automated in some applications, controls the gas flow through the flow valve 112, which subsequently exits the driver 12 through the nebulizer outlet 18. Thus, using the control knob 114, the patient or practitioner can adjust the nebulization to the desired density.

In operation, when it is desired that a patient inhale atomized medication from the portable nebulizer unit 14, the driver unit 12 is connected to a reliable supply of medical quality gas at the gas inlet 74. The first oxygen tube 20 is interconnected between the nebulizer gas outlet 18 and the nebulizer unit inlet 22, and the second oxygen tube 32 is interconnected between the sensor port 30 and the connector end of a universal sensor port adapter 46. The sensor end of the adapter 46 is inserted into the expired gas outlet port 44 of the airway device 16, until the larger diameter disk portion 62 abuts the end of the T-tube. Then the patient inserts the mouthpiece 42 into his mouth and the nebulization process is ready to commence.

An important feature of the invention is the disk 60, which is configured so that the patient may breathe through the mouthpiece 42 and airway device 16, but is breathing air at atmospheric pressure, unlike the prior art positive pressure nebulizers. This is true because the sensor end tube 50 has a smaller diameter than that of the first tubular portion 34 and expired gas outlet port 44, so that only a small portion of the air being inhaled or exhaled by the patient flows through the tube 50. The greater portion of the inhaled and exhaled gas flows directly to or from the atmosphere through the plurality of holes 66 which are bored through the entire disk 60 and extend into the port 44, in the annular portion of the port diameter which surrounds the tube 50.

When the patient takes a breath, inhaling air through the airway device 16, including atmospheric air through the holes 66, the negative pressure generated is transmitted along the length of the second oxygen tube 32, and into the interior of the driver 12, through the sensor port 30 and the sensor passage 100. This negative pressure pulls the diaphragm tip 96, which comprises a small attached plastic block in the preferred embodiment, upwardly, thereby exposing the microscopic metering apertures in each of the yoke legs 92 and 94. This permits a microscopic flow of the triggering pressure gas from gas passage 84 to exit the first metering aperture in leg 92 and to impinge on the second metering aperture in leg 94, thereafter traveling through the trigger gas passage 102 and entering the pneumatically actuated on/off valve 82 through the trigger inlet 110. This triggers the valve 82 to open and a full flow of medical quality gas to flow from the inlet passage 76, through the valve gas inlet 106 and the gas outlet 108, and then through the gas line 104 and the flow valve 112 to the nebulizer gas outlet 18.

From the nebulizer gas outlet 18, the nebulizing gas flows through the first oxygen tube 20 and into the nebulizer unit 14, via the nebulizer unit inlet 22. This causes the nebulizer to concurrently introduce nebulized medication into the airway device 16 through the first port 38, from whence it is drawn into the patient's lungs.

During exhalation, positive air pressure is introduced into the airway device 16 as exhaled gases flow through the fluid passage 58 and outwardly to atmosphere through the holes 66 in the disk 60. The positive air pressure is sensed through the second oxygen tube 32 and the sensor port 30, creating a positive pressure in the sensor passage 100 and causing the diaphragm tip 96 to move downwardly, thereby blocking the aforementioned metering apertures in the yoke legs 92 and 94. Consequently, the cessation of trigger gas flow into the valve 82 causes the valve to switch to an off condition, thereby cutting off the flow of positive pressure gas to the nebulizer 14. This, in turn, stops the flow of nebulized medication to the patient during the balance of his or her exhalation cycle, thereby ensuring that little or no medication will be wasted into the atmosphere.

As mentioned above, another important advantage of the disclosed invention is the use of a universal sensor port adapter 46, which permits the T-connection airway device 16 to be quickly and conveniently attached to the sensor port of a driver unit, and also permits the patient to breathe atmospheric air. Because of its universality, the sensor port adapter may be interchangeably utilized with any sensing nebulizer system, and, even more importantly, may be used with standard off-the-shelf T-connector airway devices.

Yet another important advantage of the invention is the use of a fluidic valve as a first stage sensor valve which triggers a pneumatically actuated on/off valve to initiate and cut off the supply of pressurized gas to the nebulizer; responsive to the inhalation/exhalation cycle of the patient. In particular, this two stage arrangement, which employs a very low flow rate first stage fluidic valve, has a sensitivity adjustable to approximately $\frac{1}{10}$ PSI. It is therefore adaptable even to weak, sick, older patients by use of a light aerosol mask fitted to their face, giving much less feeling of confinement and having much greater acceptance than prior art systems.

Still another important advantage of the invention is the ability it provides to accurately monitor and measure the quantity of medication actually being inhaled by the patient. In prior art nebulizers not having the feature of shutting off the flow of medication during exhalation, all of the medication nebulized and delivered during the exhalation cycle is wasted. This is costly, and also makes it difficult to determine a proper treatment regime in order to ascertain that the patient is receiving the right dosage of medication. However, when the medication is delivered only during the shorter inhalation cycle, a precise measurement of the dosage received, for instance, by using a sporometer, is easily obtained.

Of course, while the disclosed internal driver arrangement and the construction of valves 82 and 86 constitute the preferred embodiment, other arrangements and valve types capable of performing substantially the same function could be used equally effectively in the inventive system. Also, the inventive system could be packaged differently, e.g. by manifolding the tubes or re-designing the layout of the driver 12, without impacting the inventive concept.

The invention has particular applicability to handheld nebulizers, but may also be used for a variety of other applications. For example, the inventive principles may be equally applicable to cannulas, which supply oxygen without medication, oxygen resuscitators, and perhaps insulin inhalers as well.

Although an exemplary embodiment of the invention has been shown and described, many changes, modifications, and substitutions may be made by one having ordinary skill in the art without necessarily departing from the spirit and scope of this invention. Therefore, the invention is to be limited only in accordance with the scope of the appended claims.

What is claimed is:

1. An adapter device for use in an apparatus for delivering pressurized gas to a patient during inhalation and for preventing delivery of pressurized gas to the patient during exhalation, said adapter device being adapted to couple an airway device to a sensor port associated with a pressurized gas supply source, and comprising:

a generally tubular element having a fluid passage extending therethrough, and having a connector end adapted for insertion into an expired gas outlet port in such an airway device, and a sensor end adapted to be coupled to a proximal end of a fluid line, such a fluid line being adapted to be coupled at a distal end thereof with such a sensor port; and structure for ensuring that such an expired gas outlet port remains open to atmosphere when said connector end is inserted therein, said structure comprising a generally disk-shaped element circumscribing said tubular element between said sensor end and said connector end, the disk-shaped element having at least one hole extending therethrough, a connector end of said hole being disposed in an axially spaced relationship relative to said tubular element connector end, such that a substantial portion of said tubular element connector end may be inserted into an expired gas outlet port in order that said connector end of said hole abuts the expired gas outlet port, and the airway device is open to atmosphere through said at least one hole.

2. An adapter device as recited in claim 1, wherein said disk-shaped element has a plurality of holes bored therethrough, arranged in an annular pattern surrounding said tubular element.

3. An adapter device as recited in claim 1, wherein said disk-shaped element further comprises a first smaller diameter portion closest to the connector end of the adapter device and a second larger diameter portion closest to the sensor end of the adapter device, said at least one hole extending continuously through both of said disk diameter portions, wherein when said connector end is inserted into a expired gas outlet port, the smaller diameter disk portion enters said expired gas outlet port while said larger diameter disk portion abuts the end of said airway device.

4. An adapter device as recited in claim 3, wherein said first smaller diameter portion has a greater axial length than said second larger diameter portion.

5. An adapter device as recited in claim 1, wherein said connector end is tapered for easier insertion into a proximal end of a fluid line.

6. A system for delivering pressurized gas to a patient during the inspiratory phase and for preventing delivery of pressurized gas to a patient during the expiratory phase of a patient's respiratory cycle, said system comprising:

a pressurized gas supply device;

an airway device having a first port adapted to receive pressurized gas from said supply device, a second port adapted to receive a mouthpiece through which a patient may inhale and exhale, a third port which is open to the atmosphere, and a fluid passage interconnecting said first, second, and third ports;

a flow controller for initiating the flow of pressurized gas to said first port responsive to inhalation by a patient, and for shutting off the flow of pressurized gas to said first port responsive to exhalation by a patient; and a nebulizer unit adapted to be in-line between said pressurized gas supply device and said first port, said nebulizer unit including a reservoir for containing a supply of medication and having an inlet for receiving pressurized gas from said pressurized gas supply device, and an outlet adapted for fluid communication with said first port, through which a mixture of pressurized gas and aerosolized medication may flow for inhalation by said patient.

7. The system as recited in claim 6, and further comprising an adapter device for coupling said third port to a sensor port associated with said pressurized gas supply device, said adapter device comprising a first end adapted for insertion into the third port and a second end adapted to be coupled to said sensor port, and further comprising structure for ensuring that said third port remains open to atmosphere when said first adapter end is inserted therein.

8. The system as recited in claim 7, wherein said adapter device comprises a generally tubular element having a fluid passage therethrough, said first end comprising a connector end adapted for insertion into the third port, and said second end comprising a sensor end adapted to be coupled to a proximal end of a fluid line, the distal end of said fluid line being adapted to be coupled to said sensor port, such that said third port and said sensor port are in fluid communication through said generally tubular fluid passage and said fluid line;

wherein the structure for ensuring that the third port remains open to atmosphere when the adapter connector end is inserted therein comprises a generally disk-shaped element circumscribing said tubular element between the sensor end and the connector end, the disk-shaped element having at least one hole extending therethrough, such that when the connector end is inserted into said third port, the disk-shaped element abuts the end of the airway device and the airway device is open to the atmosphere through said at least one hole.

9. The system as recited in claim 8, wherein said disk-shaped element has a plurality of holes extending therethrough, arranged in an annular pattern surrounding said tubular element.

10. The system as recited in claim 8, wherein said disk-shaped element further comprises a first smaller diameter portion closest to the connector end of the adapter device and a second larger diameter portion closest to the sensor end of the adapter device, said at least one hole extending continuously through both of said disk diameter portions, wherein when said connector end is inserted into the airway device third port, the smaller diameter disk portion enters said airway device fluid passage while the larger diameter disk portion abuts the end of said airway device.

11. The system as recited in claim 10, wherein said first smaller diameter portion has a greater axial length than said second larger diameter portion.

12. The system as recited in claim 8, wherein said connector end is tapered for easier insertion into the proximal end of said fluid line.

13. A system for delivering pressurized gas to a patient during the inspiratory phase and for preventing delivery of pressurized gas to a patient during the expiratory phase of a patient's respiratory cycle, said system comprising:

a pressurized gas supply device;

an airway device having a first port adapted to receive pressurized gas from said supply device, a second port adapted to receive a mouthpiece through which a patient may inhale and exhale, a third port which is open to the atmosphere, and a fluid passage interconnecting said first, second, and third ports;

a flow controller for initiating the flow of pressurized gas to said first port responsive to inhalation by a patient, and for shutting off the flow of pressurized gas to said first port responsive to exhalation by a patient;

an adapter device for coupling said third port to a sensor port associated with said pressurized gas supply device, said adapter device comprising a generally tubular element having a first end adapted for insertion into the third port and a second end adapted to be coupled to said sensor port;

said generally tubular element having a fluid passage therethrough, said first end comprising a connector end adapted for insertion into the third port, and said second end comprising a sensor end adapted to be coupled to a proximal end of a fluid line, the distal end of said fluid line being adapted to be coupled to said sensor port, such that said third port and said sensor port are in fluid communication through said generally tubular fluid passage and said fluid line; and a generally disk-shaped element for ensuring that the third port remains open to atmosphere when the adapter connector end is inserted therein, said disk-shaped element circumscribing said tubular element between the sensor end and the connector end, the disk-shaped element having at least one hole extending therethrough, such that when the connector end is inserted into said third port, the disk-shaped element abuts the end of the airway device and the airway device is open to the atmosphere through said at least one hole.

14. The system as recited in claim 13, wherein said disk-shaped element has a plurality of holes extending therethrough, arranged in an annular pattern surrounding said tubular element.

15. The system as recited in claim 13, wherein said disk-shaped element further comprises a first smaller diameter portion closest to the connector end of the adapter device and a second larger diameter portion closest to the sensor end of the adapter device, said at least one hole extending continuously through both of said disk diameter portions, wherein when said connector end is inserted into the airway device third port, the smaller diameter disk portion enters said airway device fluid passage while the larger diameter disk portion abuts the end of said airway device.

16. The system as recited in claim 15, wherein said first smaller diameter portion has a greater axial length than said second larger diameter portion.

17. The system as recited in claim 13, wherein said connector end is tapered for easier insertion into the proximal end of said fluid line.

18. An adapter device for use in an apparatus for delivering pressurized gas to a patient during inhalation and for preventing delivery of pressurized gas to the patient during exhalation, said adapter device being adapted to couple an airway device to a sensor port associated with a pressurized gas supply source, and comprising:

a generally tubular element having a fluid passage extending therethrough, and having a connector end adapted for insertion into an expired gas outlet port in such an airway device, and a sensor end adapted to be coupled to a proximal end of a fluid line, such a fluid line being adapted to be coupled at a distal end thereof with such a sensor port; and structure for ensuring that such an expired gas outlet port remains open to atmosphere when said connector end is inserted therein, said structure comprising a generally disk-shaped element circumscribing said tubular element between said sensor end and said connector end, the disk-shaped element comprising a first smaller diameter portion closest to the connector end of the adapter device and a second larger diameter portion closest to the sensor end of the adapter device, said disk-shaped element having at least one hole extending continuously through both of said disk diameter portions, such that when the connector end is inserted into an expired gas outlet port, the smaller diameter disk portion enters the expired gas outlet port while said larger diameter disk portion abuts the end of the airway device, the airway device being open to the atmosphere through said at least one hole.

19. An adapter device as recited in claim 18, wherein said first smaller diameter portion has a greater axial length than said second larger diameter portion.

* * * * *